United States Patent [19]

Clifton et al.

[11] Patent Number: 4,501,271

[45] Date of Patent: Feb. 26, 1985

[54] RESUSCITATOR

[75] Inventors: John T. Clifton, Bowmanville, Canada; John W. Spear, 2686 Thornlodge Dr., Mississauga, Ontario, Canada

[73] Assignee: John William Spear, Mississauga, Canada

[21] Appl. No.: 310,731

[22] Filed: Oct. 13, 1981

[51] Int. Cl.³ .............................................. A61M 16/00
[52] U.S. Cl. .......................... 128/205.13; 128/205.24; 128/910; 137/512.2; 137/102
[58] Field of Search ............. 128/205.13, 910, 205.12, 128/204.18, 205.17; 137/102, DIG. 9, 512.2

[56] References Cited

U.S. PATENT DOCUMENTS

| | | | |
|---|---|---|---|
| 2,931,357 | 4/1960 | Arborelius et al. | 128/205.12 |
| 3,196,866 | 7/1965 | Adams | 128/205.13 |
| 3,200,818 | 8/1965 | Johannisson | 128/205.12 |
| 3,216,413 | 11/1965 | Mota | 128/205.13 |
| 3,366,133 | 1/1968 | Johannisson | 128/203.28 |
| 3,419,029 | 12/1968 | Straub | 137/102 |
| 3,424,185 | 1/1969 | Lansky et al. | 137/102 |
| 3,435,839 | 4/1969 | Elder | 137/512.2 |
| 3,795,257 | 3/1974 | Fabish et al. | 137/512.2 |
| 3,799,185 | 3/1974 | Milnes et al. | 137/512.2 |
| 4,121,580 | 10/1978 | Fabish | 128/205.13 |
| 4,239,038 | 12/1980 | Holmes | 128/205.13 |
| 4,336,798 | 6/1982 | Beran | 128/204.18 |

FOREIGN PATENT DOCUMENTS 1238650 7/1971 United Kingdom ........... 128/205.13

OTHER PUBLICATIONS

Scavenger-OR Gas Evacuator from Air Products Advertisement, 1975.

*Primary Examiner*—Richard J. Apley
*Assistant Examiner*—Harry J. Macey
*Attorney, Agent, or Firm*—George A. Rolston

[57] ABSTRACT

A two-way valve for use in breathing apparatus comprising a valve chamber having a supply end and a mask end, both ends having openings, a valve plate member of thin lightweight material freely movable within the valve chamber between the supply end and the mask end for closing respective openings, the valve plate member defining a flow axis and a generally circular opening centered on the flow axis, a plurality of support arms extending radially inwardly from the perimeter of the circular opening, the support arms defining and being joined together at a solid central hub, a plurality of stub members extending radially inwardly from the perimeter of the circular opening, a fastening boss extending from the central hub towards the mask end of the chamber, retaining flanges on the boss spaced from the valve plate, a flat planar flexible valve membrane attached to the valve plate member, the membrane having a central opening fitting elastically over the boss, and fitting between the valve plate member and the flanges, the valve membrane normally closing the sector-shaped openings, and vents in the chamber being oriented and located so as to be closed by the valve plate member, when the valve plate member is located at the mask end, the vents being opened when the valve plate member is moved away from the mask end.

9 Claims, 6 Drawing Figures

RESUSCITATOR

The invention relates to resuscitators, and in particular, to manually operable emergency devices.

BACKGROUND OF THE INVENTION

Resuscitation of accident victims, or persons suffering from a sudden illness, conventionally involves mouth-to-mouth contact with the victim. This is both tiring, and physically distasteful and, in some cases, almost impossible. For example, where the victim is located in a confined space, it may be impossible for an assistant to place his head in the necessary position.

In order to overcome some of these problems, tubular devices have been manufactured, which avoid the actual physical contact with the mouth of the victim. However, it is still necessary for the assistant to use his own lungs.

Another disadvantage of mouth-to-mouth resuscitation is the fact that the victim is not receiving clean air, but is receiving air from the lungs of the assistant. Ambient air normally contains about 22% free oxygen whereas exhaled air contains about 16% free oxygen. In addition, there is the inherent danger of the communication of disease.

Numerous devices have been proposed and are on the market, involving some form of air bag, and face mask or breathing tube or other breathing device to overcome these problems. The air bag is designed to be squeezed, at appropriate intervals, while the mask or other device is held over the face of the victim. The construction of the air bag should preferably be such that it can be squeezed with one hand.

In many cases the construction of these manual devices is relatively complex, involving the use of, for example, interior springs within the air bag, and complex valves, such that the cost of manufacture is relatively high. As a result, such manual devices have not achieved wide distribution. In many cases, their use is effectively restricted, by virtue of their high price, to professional health care services, such as ambulances, first aid points, and hospital emergency rooms.

This is unfortunate, since of course such emergency equipment should preferably achieve mass distribution, so that it is immediately available. For example, it would be desirable to include such emergency devices in all first aid kits carried on boats, trucks, automobiles, work sites, and recreation centres and in the home.

In addition, such emergency devices as are presently on the market, have incorporated relatively complex valve systems, so as to control the flow of air into and out of the breathing mask. The function of such emergency devices is, of course, to ensure that fresh air is supplied to the victim, and that air exhaled by the victim is vented to atmosphere and is not returned to the air bag. In order to achieve this result it is necessary to have an air flow valve which permits air to flow from the bag into the mask, but which prevents return flow, and in addition, a further valve which permits air to flow from the mask to atmosphere, but which does not permit air to flow from the bag to atmosphere, since otherwise there would be no air pressure sufficient to inflate the lungs of the victim.

The design and construction of valving systems in such prior art devices has been relatively complex, which has been one of the factors in the relatively high cost involved. In addition to this, however, if the victim should discharge water or vomit into the face mask, there is a strong possibility that one of the valves will fail.

For these reasons it is desirable to both simplify the construction of the valve, and also avoid the use of small components, springs and the like, which may be a source of trouble.

A further factor limiting the use of prior art breathing devices has been the need for sterilization. In most cases this has been achieved simply by having a replaceable face mask. However, since the victim will in fact be breathing in and out through the tubing and valve systems, these too should preferably be either sterilized or replaceable. In practice, however, this requirement has not been met.

Sterilization of components is relatively time consuming, and unless trained personnel are available, it will not be carried out satisfactorily. In addition, it requires components which are made of materials capable of withstanding high temperatures, and which must be easily dismantled and reassembled. This greatly increases the expense and, in addition, introduces the further possibility that the parts may be reassembled in the wrong way, so that the device does not function at all.

For all of these reasons, it is considered highly desirable to produce a low-cost, simple, economical emergency breathing device of the type described, which is intended for a one-time use only, and is then simply discarded and replaced with a new one. It is also desirable to greatly simplify the function of the valve, and keep the components relatively large, and eliminate the use of springs, so that if during use, some obstruction should interfere with the operation of the valve, it can readily be removed.

BRIEF SUMMARY OF THE INVENTION

The invention seeks to overcome the foregoing disadvantages, by the provision of a resuscitator comprising a manually operable air bag, having a fresh air inlet means for admitting fresh air to the interior of the bag, and a two-way valve means connected with said bag, and adapted to receive air from said bag, said valve means including a valve chamber having a bag end and a mask end, said mask end being adapted for communication with a suitable face mask, and having a valve plate member freely moveable within said valve chamber between said bag end and said mask end, openings formed through said valve plate member, a flexible resilient valve element attached to said plate member, and normally covering said openings, and being moveable so as to expose said openings when air flows from said bag end of said chamber, and vent opening means in said chamber adjacent said mask end, said vent opening means being oriented and located so as to register with portion of said valve plate member when the same is located at said mask end, thereby sealing the same against escape of air to atmosphere, said vent openings being opened when said plate member is moved away from said mask end towards said bag end of said chamber.

More particularly, it is an objective of the invention to provide a resuscitator having the foregoing advantages, wherein the chamber is formed of two-part construction, and is permanently sealed together to prevent disassembly.

More particularly, it is an objective of the invention to provide a resuscitator having the foregoing advantages wherein the valve means has a bag end connection member having a predetermined shape and dimension, adapted for interconnection with said bag, and further has a mask end connection member having a predetermined shape and dimension different from said bag end connection member, for interconnection with a suitable mask.

More particularly, it is an objective of the invention to provide a resuscitator having the foregoing advantages, wherein the fresh air intake means for said bag incorporates a valve member identical to said valve plate member in said valve chamber, whereby to simplify construction and reduce manufacturing costs.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention.

IN THE DRAWINGS

Figure 1:
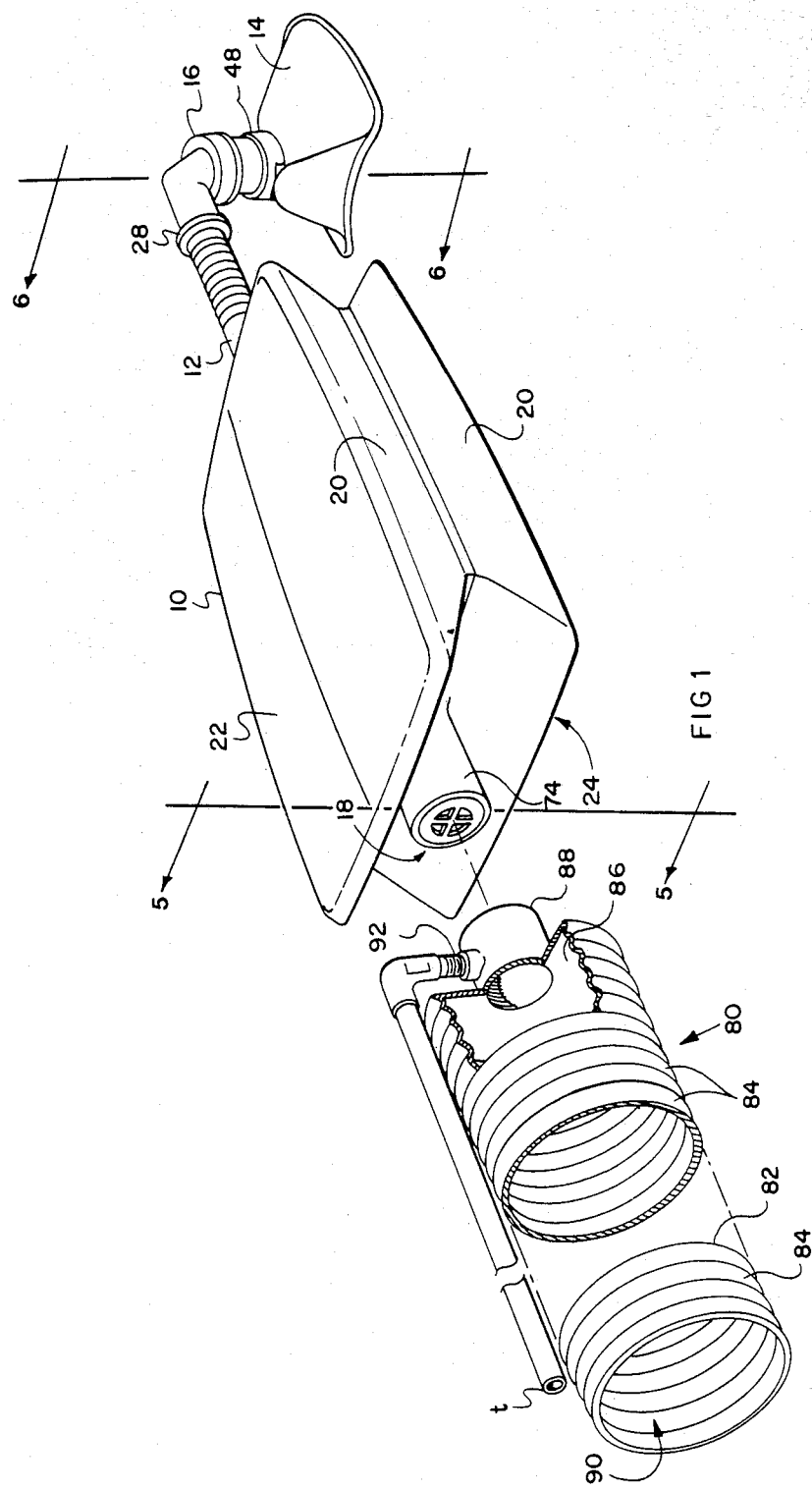
FIG. 1 is a perspective of a resuscitator according to the invention, shown provided with a face mask ready for use.
Figure 2:
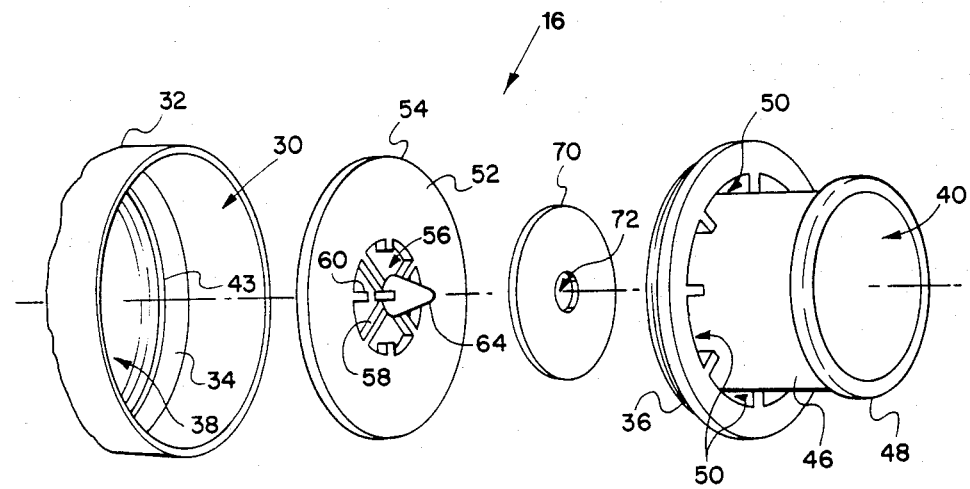
FIG. 2 is an exploded perspective illustration of the valve means and valve chamber.
Figure 3:
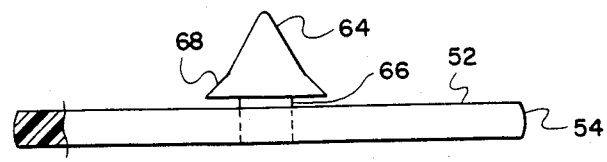
FIG. 3 is an elevation of a portion of the valve means.

Referring now to FIG. 1, the resuscitator according to the invention will be seen to comprise a generally rectangular-shaped bag 10, a flexible hose 12, a mask 14, and an outlet valve 16. An inlet valve 18 is located at the end of the bag opposite to the hose 12. The bag 10 is formed with a single concertina-like fold 20 in its side walls, whereby the bag may flex. It also has generally flattened upper and lower walls 22-24. The single, indented channel-like fold permits flexing, while being resistant to distension due to air pressure.

Bag 10 is formed of flexible thermoplastic material, and is preferably manufactured economically by blow molding techniques. In the preferred form as shown, the bag has dimensions such that it may be grasped in one hand and squeezed between the four fingers and thumb. In this way, it is possible for a single operator to both operate the bag 10, and at the same time, with the other hand, hold the mask 14 over the face of the victim.

The hose 12 is formed in this particular construction integrally with bag 10, and is preferably flexible to some degree. The end of the hose 12 terminates in a female socket joint 28 having a predetermined diameter and shape for reasons to be described.

Other breathing devices such as a tube or the like may be used in place of the mask in some circumstances.

Referring now to FIGS. 2, 3, 4 and 6, the outlet valve 16 will be seen to comprise a valve chamber indicated generally as 30, and formed by cylindrical side wall 32, and having a bag end formed by the generally annular wall portion 34, and having a mask end formed by the generally annular wall portion 36. Wall portion 34 defines a through opening 38 for passage of air from the bag, and wall portion 36 defines a through opening 40 for passage of air to the mask. A bag connection member 42 is connected to the side wall 34, and has a predetermined shape and dimension to make a snug snap fit within connection socket 28 of hose 12. A sealing ring or rib 43 is formed on wall portion 34, and two similar concentric sealing rings or ribs 44 and 45 are formed on wall portion 36.

A mask end connection member 46 is attached to chamber end wall 36, and is adapted to make a snug fit within a female socket member 48 of mask 14.

Connector portions 42 and 46 are of different sizes, and sockets 28 and 48 are of different sizes, so that they cannot be connected in the reverse direction.

They are, however, of such a design that they can readily be pulled apart, in the event of the valve chamber 30 receiving any contaminants.

Annular end wall 36 is provided with a plurality of spaced-apart vent openings 50, located between sealing rings 44 and 45.

Located within valve chamber 30 is a valve plate member 52. Plate member 52 is of generally circular flat disc-like construction, having an outer periphery 54, and having a generally bevelled profile. Plate member 52 has a diameter slightly less than the interior diameter of chamber 30, and is freely moveable therein without restriction.

Four openings 56 are formed through the center of disc member 52, being spaced apart by radial struts 58. Additional radial stub members 60 are located equally spaced between struts 58 for reasons to be described below.

On the side of disc member 52 facing the mask opening 40, a generally central conical boss 64 is provided, being mounted on a reduced diameter stem 66, which extends normal to the central intersection of struts 58. A pair of generally triangular flanges 68 are formed on opposite sides of conical boss 64 for reasons to be described.

In order to permit only one-way air flow through openings 56, a flexible resilient valve element 70 is provided. Valve element a membrane formed on thin flexible rubber material, or other suitable flexible material, and has a central opening 72. Boss 64 is adapted to be forced through central opening 72, and the disc 70 then stretches to permit the flanges 68 to pass therethrough, after which it snaps around stem 66. In this way the valve element 70 is held in position covering the openings 56.

In order to maximize air flow through the relatively small cross-sectional area available, the openings 56 are generally sector-shaped, or wedge- or pie-shaped, with their outer arcuate edges lying on the perimeter of a circle. Although four sector-shaped openings (each being generally quadrant-shaped) are illustrated, it is not intended to exclude the possibility of using a greater or lesser number of openings having a greater or lesser arcuate extent.

Figure 4:
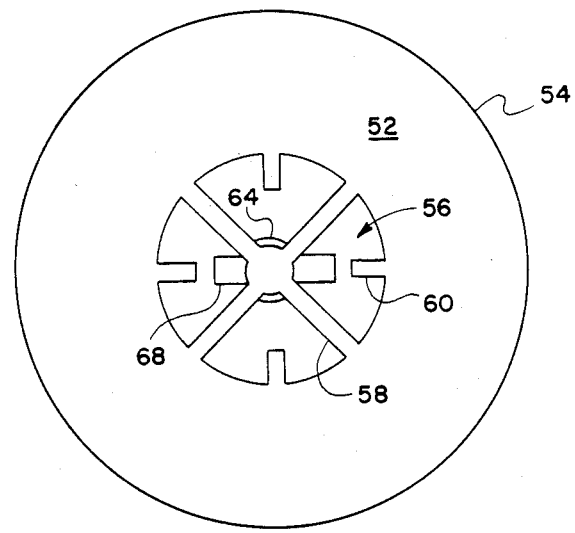
FIG. 4 is a plan of FIG. 3.

It will also be appreciated that because struts 58 meet at a central intersection, they in effect form a central hub. As shown in FIG. 4, the central hub may have a diameter somewhat larger than the width of struts 58. However, in order to maximize air flow, the diameter of the central hub is preferably as small as possible.

It will be noted that the valve element 70 is located on the mask side of valve plate member 52.

Cylindrical wall 32 is bonded to end wall 36. In this way valve chamber 30 is permanently closed, rendering the valve plate 52 inaccessible and tamper proof.

Any suitable form of face mask, such as that shown as 14 is provided, and a variety of different masks may be provided for different patients or victims, as the case may be.

Figure 5:
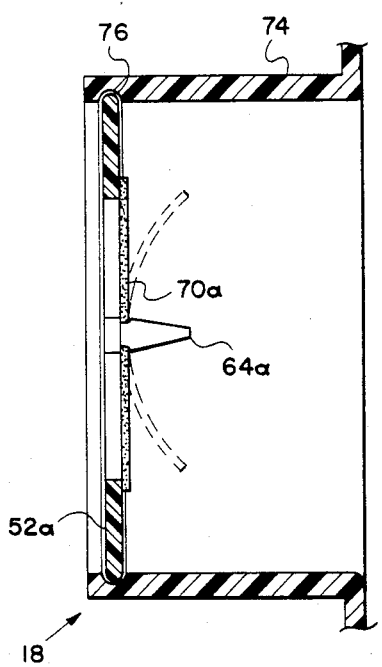
FIG. 5 is an enlarged section along the line 5—5 of FIG. 1, showing the intake valve, and, FIG. 6 is an enlarged section along the line 6—6 of FIG. 1 showing the outlet valve.

In order to permit fresh air to enter bag 10, the inlet valve 18 will be seen, from FIG. 5, to comprise a generally cylindrical tubular body portion 74, having an interior groove 76. Received within the groove 76 is a valve plate member 52a, identical to valve disc member 52 of the valve 16, and having the same radial struts 58a, boss 64a and flanges 68a. An identical flexible resilient valve element 70a is located on the bag side of plate member 52a.

Figure 6:
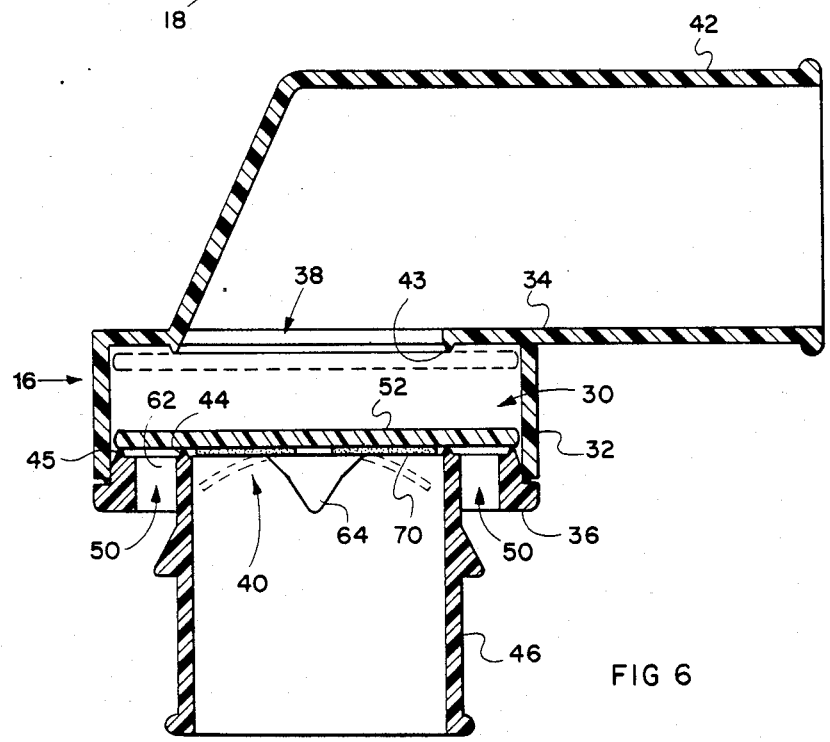

In operation, after the victim has been suitably prepared and positioned, and any foreign matter has been cleared from his mouth and breathing passages, in accordance with established resuscitation techniques, the mask 14 is then placed over the victim's nose and mouth. The bag 10 is then grasped between four fingers and thumb of one hand, and squeezed. Air contained within the bag 10 will then be forced along the hose 12 into valve 16. As air enters valve chamber 30, the valve plate member 52 will normally be lieing on the wall portion 36. In this position the plate member covers the vent openings 50, so that air cannot escape. Air pressure from the bag will then deflect resilient valve element 70, as shown in FIG. 6. Air can thus pass through the openings 56, through the mask connection portion 46 and into the mask, and thus into the victim's mouth and nose, and lungs.

Pressure on the bag is then relaxed, and the bag will then expand to its normal extended position as shown in FIG. 1, inducting fresh air through inlet valve 18. This is achieved simply by the negative pressure in the bag 10 itself causing the valve element 70a on plate member 52a to deflect essentially as shown in FIG. 5, thereby allowing air to pass through plate member 52a into the bag.

At the same time, air in the victim's lungs will be expelled back into the mask. This will produce a reverse flow of air within chamber 30—i.e. from the mask towards the bag. This will cause plate member 52 to lift off wall 36, and move upwardly within chamber 30 against wall 34 as shown in FIG. 6 in phantom. In this position, the plate member 52 closes off the opening 38 so that air cannot flow into the bag.

Note that in the two positions of valve plate 52, the plate makes sealing engagement either with rings 44 and 45, or with ring 43.

This avoids all over contact with either end wall 36, or end wall 34.

Air vented from the lungs of the victim is, however, free to pass into chamber 30 and out through vent openings 50 to atmosphere.

This cycle of operations will then be continued with the operator simply squeezing and releasing the bag in timed relation to the victim's breathing. If the victim is having difficulty in exhaling, it may be desirable to apply gentle pressure to the rib cage, in accordance with the usually established resuscitation techniques.

In the event that the patient ejects water or vomit into the mask 14 or valve 16, it may be cleaned simply by momentarily removing the mask from the victim and squeezing the bag vigorously to eject the material.

If for some reason the mask and/or valve chamber are disconnected, it will be seen that due to the differences in sizes between connection members 42 and 46, it is impossible to reassemble the resuscitator with the valve and mask the wrong way around.

In addition, due to the two-part construction of the valve 16, the valve plate member 52 is permanently retained within chamber 30, so that it cannot be disassembled, and inadvertently replaced the wrong way round.

The design of the valve member is such that a tendency to stick or join in the chamber is minimized, by the radiussing of its periphery, and also by the use of the raised seating rings in the valve chamber.

From this description of the invention it will be seen that the construction techniques involved are low cost and economical, such that it should be possible to produce the entire unit and sell it for a one-time usage only, so that after use it may simply be discarded, and a fresh one made ready for the next victim.

In this way the need for disassembly, sterilization and reassembly is completely avoided. In this way it becomes possible to use lower cost materials in construction, without any loss of the essential utility and function of the device.

Where extra oxygen is available, and it is felt desirable to use it, then an oxygen supply chamber 80 may be attached to inlet valve 18. Chamber 80 consists of a tubular side wall 82, preferably having a volume at least equal to bag 10, and having pleats or folds 84 to facilitate storage. At its downstream end chamber 80 has an end wall 86, and a connection collar 88, adapted to fit over cylindrical member 74 of inlet valve 18.

The upstream end of sidewall 82 defines an opening 90, open to atmosphere.

An oxygen supply tube t may be connected to nipple 92 on collar 88.

In this mode of operation oxygen is supplied from a suitable source, e.g. a cylinder (not shown), and any necessary pressure reducer and/or flow regulator to tube t. Oxygen will flow continuously into chamber 80. Each time the bag 10 is operated oxygen is drawn into the bag via inlet valve 18. Some atmospheric air may be drawn into chamber 80, and may thus mix with the oxygen, so that the bag 10 is charged with essentially oxygen enriched air, rather than with pure oxygen. The degree of such mixing will of course vary depending on factors such as the oxygen flow rate, and breathing rate and volume of the victim.

While oxygen may typically be added to the air supply in this way, any other additive could be supplied or mixed. Such additives might include other gases, or medication of various kinds. Clearly in some cases some form of flow metering device can be employed such as is well known in the art.

The foregoing is a description of a preferred embodiment of the invention which is given here by way of example only. The invention is not to be taken as limited to any of the specific features as described, but comprehends all such variations thereof as come within the scope of the appended claims.

What is claimed is:

1. A two-way valve for use in breathing apparatus such as a resuscitator of the type having a supply such as an air bag and breathing device such as a mask, tube, or the like and comprising;

a valve chamber having a supply end and a mask end, said mask end being adapted for communication with a breathing device, both said ends having opening means;

a valve plate member of thin, lightweight material freely movable within said valve chamber between said supply end and said mask end for closing respective said opening means, the valve plate member defining a flow axis and a single generally circular opening centered on the flow axis and being otherwise imperforate;

a plurality of support arms formed integrally with the plate member extending radially inwardly from the perimeter of the circular opening, the support arms defining and being integrally joined together at a solid central hub at the center of said circular opening, whereby the support arms divide said generally circular openings;

a plurality of stub members formed integrally with the plate member extending radially inwardly from the perimeter of the circular opening and terminating short of said center hub;

said support arms and said stub members lying in a common plane with the valve plate member whereby to define a flat planar valve surface;

a fastening boss formed integrally with the central hub and extending towards said mask end of said chamber;

retaining flange means formed integrally with said boss and spaced from said valve surface a predetermined distance;

a flat planar flexible valve element membrane attached to said valve plate member, said membrane having a single central opening and being otherwise imperforate and fitting elastically over said boss, and fitting within said predetermined spacing between such valve plate member and such flange means engaging such valve element membrane and retaining same in position lying flat on said flat planar valve surface; said valve element membrane normally closing said generally circular opening, and being flexibly movable so as to open said generally circular opening when air flows from said supply end opening means of said chamber to said mask end opening means, and, vent means in said chamber being oriented and located so as to be closed by said valve plate member, thereby sealing the same against escape of air to atmosphere when said valve plate member is located at said mask end of said chamber, said vent means being opened when said valve plate member is moved away from said mask end, thereby permitting venting of air to atmosphere.

2. A two-way valve as claimed in claim 1 including spacer means formed within said valve chamber around said supply end opening means, said spacer means being dimensioned to interengage with said valve member, and prevent contact thereof with said supply end.

3. A two-way valve as claimed in claim 1 wherein said vent means are formed in said chamber around said mask end opening, and including sealing means extending around said vent means, engageable by said valve plate member, for closing both said vent means and said mask end opening, whereby to prevent passage of air through said vent means, said valve member being movable away from said sealing means to permit venting of stale air through said vent means.

4. A two-way valve as claimed in claim 3 wherein said mask end opening is of circular shape of predetermined diameter, and wherein said sealing means comprises at least one annular raised rib concentric with said mask end opening, and wherein said vent means are located in a generally circular path outside said sealing means, and including further sealing means comprising an annular raised rib concentric with said first mentioned sealing means, and located radially outwardly of said vent means, whereby said two sealing means together seal said vent means and said mask end opening from one another, and from said chamber, when said valve member is lying thereon.

5. A two-way valve as claimed in claim 4 wherein said valve plate member is a circular disc, the flow axis of the valve plate member being located at the center of the valve plate member and wherein said valve element membrane is a circular disc, and has a predetermined diameter which is less than the diameter of said opening at said mask end of said chamber, whereby said valve element membrane may flex into said mask end opening, in response to passage of air.

6. A resuscitator for use with a breathing device such as a mask, tube or the like comprising;

an air bag having fresh air inlet means for admitting fresh air to the interior of the bag and having air outlet means and operable to pump air through said outlet means;

a two-way valve chamber having a supply end and a mask end, the mask end being adapted for communication with a breathing device, both said ends having opening means, the supply end opening being connectible with said air outlet means of said bag, and adapted to receive air from said bag;

a first valve plate member of thin lightweight material of predetermined shape and size freely movable within said valve chamber between said supply end and said mask end for closing respective said opening means, the first valve plate member defining a flow axis and a single generally circular opening centered on the flow axis and being otherwise imperforate;

a plurality of support arms formed integrally with the first plate member extending radially inwardly from the perimeter of the circular opening, the support arms defining and being integrally joined together at a solid central hub at the center of said circular opening, whereby the support arms divide said generally circular opening;

a plurality of stub members formed integrally with the first plate member extending radially inwardly from the perimeter of the circular opening and terminating short of said central hub;

said support arms and said stub members of said first valve plate member lying in a common plane whereby to define a flat planar valve surface;

a fastening boss formed integrally with the central hub of said first plate member and extending towards said mask end of said chamber;

retaining flange means formed integrally with said boss and spaced from said valve surface a predetermined distance;

a flat planar flexible valve element membrane attached to said first valve plate member, said member having a single central opening and being otherwise imperforate and fitting elastically over said boss and fitting within said predetermined spacing between such first valve plate member and such flange means engaging such valve element membrane and retaining same in position lying flat on said flat planar valve surface; said valve element membrane normally closing said generally circular opening and being flexibly movable so as to open said generally circular opening when air flows from said supply end opening means of said chamber to said mask end opening means, and, a second valve plate member integrally formed with support arms, a central hub, stub members, fastening boss, and flange means all being generally identical to the first valve plate member and corresponding support arms, central hub, stub members, fastening boss, and flange means, the second valve plate member having a flat planar flexible valve element membrane attached thereto generally identical to the membrane attached to the first valve plate member, the second valve plate member forming part of the air inlet means whereby to permit air flow through the inlet means into the air bag and to prevent flow out of the bag.

7. A resuscitator as claimed in claim 6 wherein said air inlet means of said air bag comprises a generally cylindrical tubular body member, including an annular groove formed around the interior of said cylindrical body, said second valve plate member being of generally circular disc-like shape, and making a pressure fit in said annular groove.

8. A resuscitator as claimed in claim 7 wherein said air outlet means comprises a generally cylindrical tubular body portion, said air inlet and air outlet means having different diameters, whereby to prevent misuse.

9. A resuscitator as claimed in claim 6 wherein said first valve plate member is movable within said valve chamber to permit flow of air through said valve chamber in response to operation of said air bag, and being movable into another position in said chamber whereby to restrict flow of air back into said air bag when said air bag is released.

* * * * *